(12) United States Patent
Hoglund et al.

(10) Patent No.: US 6,648,905 B2
(45) Date of Patent: Nov. 18, 2003

(54) ENHANCED MEDICAL THERMAL ENERGY EXCHANGE PAD

(75) Inventors: Michael R. Hoglund, Mead, CO (US); Kerri Record, Boulder, CO (US); Gary Allen Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 0 days.

(21) Appl. No.: 10/087,534

(22) Filed: Feb. 27, 2002

(65) Prior Publication Data

US 2003/0163180 A1 Aug. 28, 2003

(51) Int. Cl.$^7$ ................................................. A61F 7/00

(52) U.S. Cl. .................... 607/104; 607/108; 607/112

(58) Field of Search ................... 607/96, 104, 108–112

(56) References Cited

U.S. PATENT DOCUMENTS

| | | |
|---|---|---|
| 2,250,325 A | 7/1941 | Barnes |
| 2,726,658 A | 12/1955 | Chessey |
| 3,091,242 A | 5/1963 | Johnson, Jr. et al. |
| 3,867,939 A | 2/1975 | Moore et al. |
| 3,995,621 A | 12/1976 | Fletcher et al. |
| 4,108,146 A | 8/1978 | Golden |
| 4,114,620 A | 9/1978 | Moore et al. |
| 4,118,946 A | 10/1978 | Tubin |
| 4,149,541 A | 4/1979 | Gammons et al. |
| 4,154,245 A | 5/1979 | Daily |
| 4,919,134 A | 4/1990 | Streeter |
| 4,962,761 A | 10/1990 | Golden |
| 5,062,414 A | 11/1991 | Grim |
| 5,097,829 A | 3/1992 | Quisenberry |
| 5,133,348 A | 7/1992 | Mayn |
| 5,190,032 A | 3/1993 | Zacoi |
| 5,304,213 A | 4/1994 | Berke et al. |
| 5,383,919 A | 1/1995 | Kelly et al. |
| 5,411,541 A | 5/1995 | Bell et al. |
| 5,411,542 A * | 5/1995 | Jensen ........................ 607/104 |
| 5,466,250 A | 11/1995 | Johnson, Jr. et al. |
| 5,470,353 A | 11/1995 | Jensen |
| 5,486,207 A | 1/1996 | Mahawili |
| 5,514,169 A | 5/1996 | Dickerhoff et al. |
| 5,545,194 A | 8/1996 | Augustine |

(List continued on next page.)

FOREIGN PATENT DOCUMENTS

| WO | WO 99/44552 | 9/1999 |
|---|---|---|

*Primary Examiner*—Roy D. Gibson
(74) *Attorney, Agent, or Firm*—Marsh Fischmann & Breyfogle LLP

(57) ABSTRACT

An inventive medical thermal exchange pad is provided that includes a pliable fluid containing layer and at least a first plurality of adjacent fluid channels of coincidental configurations with the fluid containing layer. A second plurality of fluid channels may also be provided in the fluid containing layer, wherein the second plurality of fluid channels are of coincidental configurations different than those of the first plurality of fluid channels. The pad may be defined to include a central segment with one or more flap segments separately and pivotably interconnected to the central segment. In particular, a plurality of side flap segments may be provided, wherein U-shaped portions of one of the first and second plurality of fluid channels extend through at least one of the side flap segments. Further, end flap segment may be provided. In one embodiment, fluid inlet and outlet ports to/from fluid circulation layer may be disposed in the end flap segment. Dual right side and left side pads having the noted features may be adapted for use on the back region of a patient. In such applications, separated side flap segments may extend around upper back-to-outside shoulder, the ribcage and lower back-to-hip/buttocks regions of a patient. The end flap segment may extend from the scapula to top shoulder region of a patient.

37 Claims, 8 Drawing Sheets

U.S. PATENT DOCUMENTS

| | | |
|---|---|---|
| 5,609,620 A | 3/1997 | Daily |
| 5,658,325 A | 8/1997 | Augustine |
| 5,662,695 A * | 9/1997 | Mason et al. ................. 607/96 |
| 5,733,318 A | 3/1998 | Augustine |
| 5,806,335 A * | 9/1998 | Herbert et al. ................ 62/434 |
| 5,887,437 A | 3/1999 | Maxim |
| 5,913,849 A | 6/1999 | Sundström et al. |
| 6,117,164 A | 9/2000 | Gildersleeve et al. |
| 6,197,045 B1 | 3/2001 | Carson |
| 6,238,427 B1 | 5/2001 | Matta |

* cited by examiner

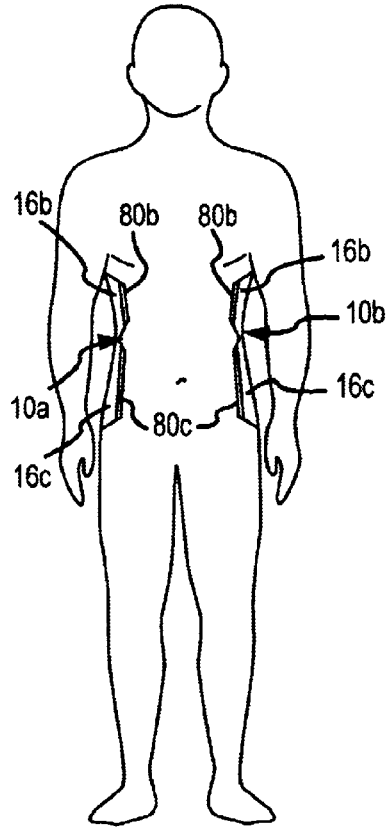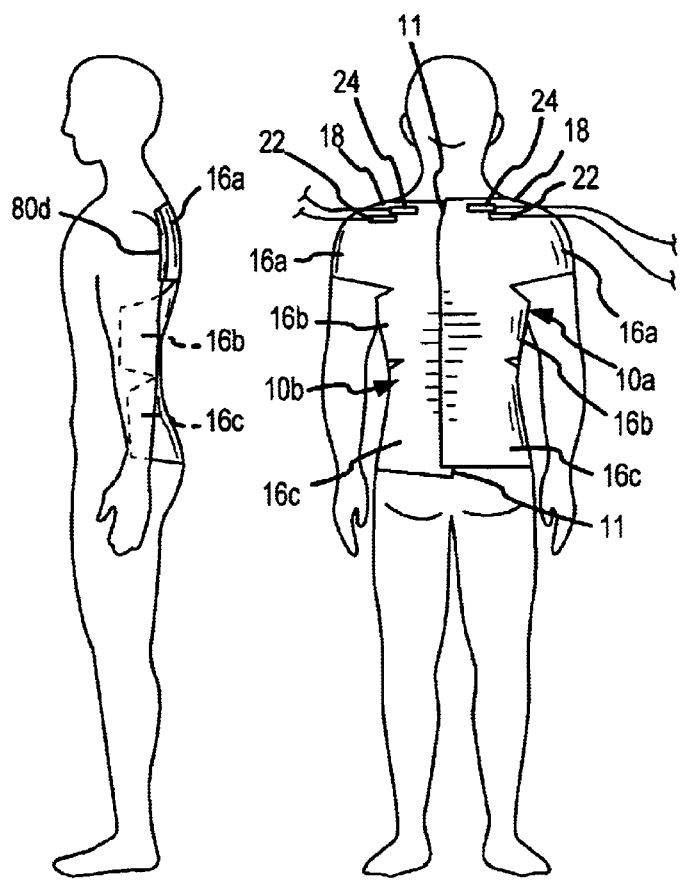
FIG.6A  FIG.6B  FIG.6C

ENHANCED MEDICAL THERMAL ENERGY EXCHANGE PAD

FIELD OF THE INVENTION

The present invention relates to medical pads, and more particularly, to medical pads utilized for thermal energy exchange with a patient. The invention is particularly apt pads utilized on the back region of a patient.

BACKGROUND OF THE INVENTION

Increasingly, medical pads are being employed to achieve thermal exchange with patients. For example, medical pads have been widely employed to address emergency hypothermia or hyperthermia patient conditions. More recently, it has also been recognized that medical pads may be employed in conjunction with surgical procedures where selected thermal regulation of a patient is desired. For example, in procedures involving the exposure of bodily organs selective heating of the patient may be desirable.

To achieve thermal regulation in many medical pad systems, a heated or cooled fluid (e.g. air or water) is circulated through one or more pads which are contacted with a patient to affect surface-to-surface thermal energy exchange. As may be appreciated, the effectiveness of such thermal exchange is partially dependent upon the extent and intimacy of skin contact. In this regard, the establishment of the desired skin interface can be compromised where medical pads extend across bodily portions of differing complex configurations.

Additionally, the effectiveness of thermal exchange is partially dependant upon the maintenance of a desired thermal gradient across the medical pad-to-patient thermal exchange interface. In this regard, it should be noted that the maintenance of a predetermined rate of fluid circulation through the pad across the intended thermal exchange interface is important to achieving the desired thermal gradient.

SUMMARY OF THE INVENTION

In view of the foregoing, a primary objective of the present invention is to provide a medical thermal energy exchange pad that provides for enhanced maintenance of a desired thermal gradient across a pad-to-patient thermal exchange interface.

An additional objective of the present invention is to provide a medical thermal energy exchange pad that provides for an improved interface across bodily portions of different complex configurations.

It is further objective of the present invention to provide a medical thermal exchange pad that accommodates patient comfort during use.

Yet another objective of the present invention is to provide a medical thermal exchange pad that is relatively easy for medical personnel to utilize, that enhances fluid circulation reliability, and that otherwise reduces potential obstructions to patient medical care.

One or more of the above objectives and additional advantages are realized by the medical thermal exchange pad of the present invention. The inventive pad includes a pliable fluid containing layer for containing a fluid circulated from a first port to a second port of the fluid containing layer. The inventive pad further includes at least a first plurality of adjacent fluid channels, disposed within the fluid containing layer, wherein the first plurality of adjacent fluid channels have first coincidental configurations. The provision of multiple channels of coincidental configurations facilitates the maintenance of a desired thermal gradient across the pad-to-patient interface, e.g. since any patient pressure occlusion within the fluid containing layer can be localized and fluid flow shunting can be minimized.

In one aspect of the inventive pad, the first plurality of fluid channels may have coincidental, serpentine configurations. Further, the pad may include a second plurality of adjacent fluid channels within the fluid containing layer. In conjunction with such aspect, the second plurality of fluid channels may have second coincidental configurations different than said coincidental, serpentine configurations of the first plurality of fluid channels. The provision of at least two different sets of fluid channels having corresponding coincidental configurations which are different enhances the ability to adapt the pad to conform to bodily portions of differing complex configurations, while also providing for a highly reliable and efficient degree of thermal exchange with a patient.

In another aspect, the inventive pad may include a second plurality of adjacent fluid channels, wherein the first and second plurality of fluid channels are disposed in series for the passage of fluid therethrough between the first and second ports of the fluid containing layer. In conjunction with this aspect, the inventive pad may further include intermediate fluid staging chamber for receiving fluid from one of the first and second plurality of fluid channels and distributing such fluid into the other of the first and second plurality of fluid channels. For such purposes, the first and second plurality of fluid channels may each have ends which terminate at the intermediate fluid staging chamber. Such an arrangement further facilitates the provision of a relatively even fluid flow through the various regions of the medical pad.

In an additional aspect, the inventive pad may include a central segment and first and second side flap segments that are separately and pivotably interconnected to the central segment. In one arrangement, the end flap segment is pivotable about a pivot axis that is transverse to pivot axes of the side flap segments (e.g. at an angle of between about 70° to 110°). Further, the first plurality of fluid channels may be disposed so that each of the channels include a U-shaped portion located in one of the first and second side flap segments. Such segmentation and channeling features further facilitate the ability to achieve conformal positioning of the inventive pad on bodily portions having differing complex configurations.

In yet a further aspect, the fluid containing layer of the inventive pad may include a central segment, at least one side flap segment pivotably interconnected to a central segment, and at least one end flap segment pivotably interconnected to the central segment. Additionally, the first and second ports of the fluid containing layer may be advantageously disposed within the end flap segment. Such positioning of the ports facilitates pad positioning on a patient, the ready establishment and maintenance of open fluid interconnections, and the localization of potential obstructions to medical personnel attending a patient. Further, the end flap segment may be pivoted relative to the central segment of the fluid containing layer so as to dispose the first and second ports away from bodily regions that may contact a patient support surface during medical procedures, thereby enhancing client comfort.

As will be appreciated, the various above-noted aspects of the present invention may be employed in various combinations. Further, additional related features may be employed with such aspects and combinations thereof.

In particular, the noted first plurality of channels may be of a substantially 1common length, e.g. within about 15% of an average length thereof, as measured along their respective center paths. Similarly, each of the first plurality of channels may also have a substantially common average width, e.g. within about 25% of an average of their average widths. Similarly, where a second plurality of channels are included, such channels may be of a substantially common length, e.g. within about 15% of an average length thereof, as measured along their respective center paths. The second plurality of channels may also have a substantially common average width, e.g. within about 25% of an average of their average widths. As may be appreciated, the provision of substantially common lengths within each channel set yields a substantially equal pressure drop from one end to the other of each of the channels comprising a given set. Further, the provision of substantially common widths further equalizes pressure drops and reduces flow shunting.

Where a first and a second plurality of channels are included in the inventive pad, one of the channel sets may be provided within an average channel width that is significantly greater than an average channel width of the other set. For example, the average width of a first plurality of channels may be established to be at least 5 times greater, and preferably between about 10 to 25 times greater than an average channel width of a second plurality of channels.

In a further feature, the inventive pad may be provided with fluid ports that are oriented to extend laterally away from a central segment. Additionally, such ports may be elongated and oriented to extend in substantially parallel co-relation. Such port orientation features can be implemented to reduce fluid line blockage considerations and facilitate patient access/comfort. Further, the ports may be provided with port members that are tapered to facilitate fluid flow and further enhance patient comfort.

The above-noted features of the present invention are particularly apt for implementation in medical thermal exchange back pads. In particular, a pair of back pads may be provided having central segments adapted for positioning on the right and left sides of a patient's spine. Such an approach facilitates use of the pads on a wide range of patient sizes, and accommodates sequential positioning of the pads on a prone patient (e.g. by rolling the patient onto one shoulder then the other). The pads may further include a plurality of side flap segments that may be pivotably positioned relative to the central segments to accommodate positioning across the shoulder region, rib-cage region and/or back-to-hip/buttocks region of a patient. Additionally, a top end flap segment may be provided for pivotable positioning from the scapula to top shoulder region of a patient.

In one back pad embodiment, each of the back pads may be provided with fluid ports disposed in the corresponding end flap segments. More particularly, such ports may be of an elongated configuration and may be oriented to extend away from a patient, e.g. substantially parallel to the pivot axes corresponding with the end flap segments.

To facilitate securement of the back pads to a patient, an adhesive surface may be provided across one side of the pads. Preferably, such adhesive surface extends across a majority and preferably all of the patient-facing side of the pad. The adhesive surface may be advantageously defined by a conformable, thermally-conductive layer (e.g. a hydrogel layer). Further, adhesive strips with removable liners may be disposed along the outer side edges of the side flap segments and the top edge of the end flap segments of the pads. As may be appreciated, the liners on such adhesive strips may be selectively removed in conjunction with the liners provided on the above-noted conformable layer during positioning of the pads.

In addition to the noted features, the inventive pad may incorporate various teachings of U.S. Pat. No. 6,197,045 entitled "COOLING/HEATING PAD AND SYSTEM", and U.S. patent application Ser. No. 09/476,850 entitled "COOLING/HEATING PAD AND SYSTEM", filed Jan. 3, 2000, each hereby incorporated by reference in its entirety.

Additional aspects and advantages of the present invention will become apparent to those skilled in the art upon consideration of the further description provided hereinbelow.

BRIEF DESCRIPTION OF THE DRAWINGS

FIGS. 6A, 6B, 6C illustrate bodily front, side and back views, respectively, of the embodiment of FIGS. 1 and 2 positioned on the back of a patient.

DETAILED DESCRIPTION

Figure 1:
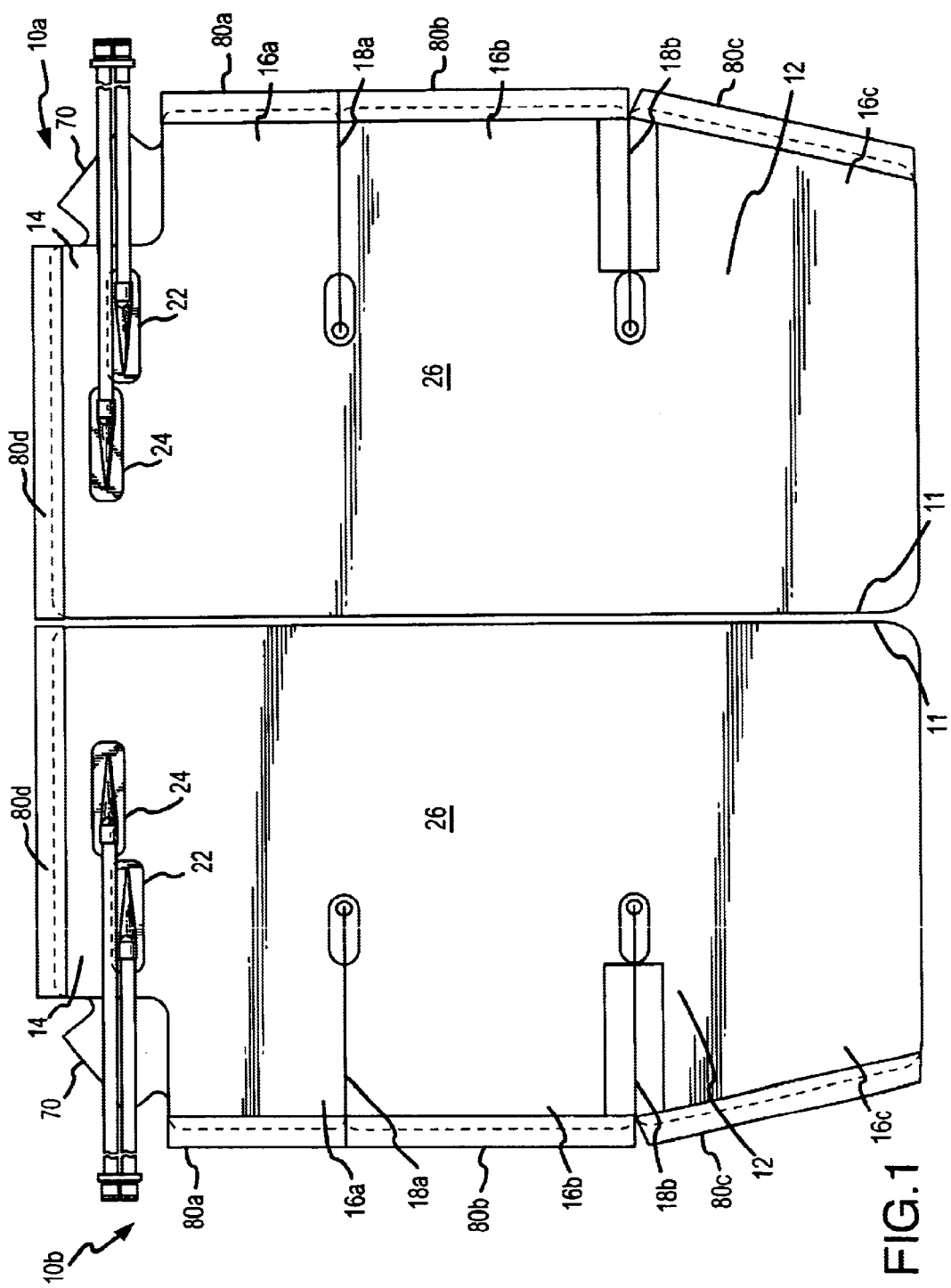
FIG. 1 is a plan view of right and left back pads comprising one embodiment of the present invention.
Figure 2:
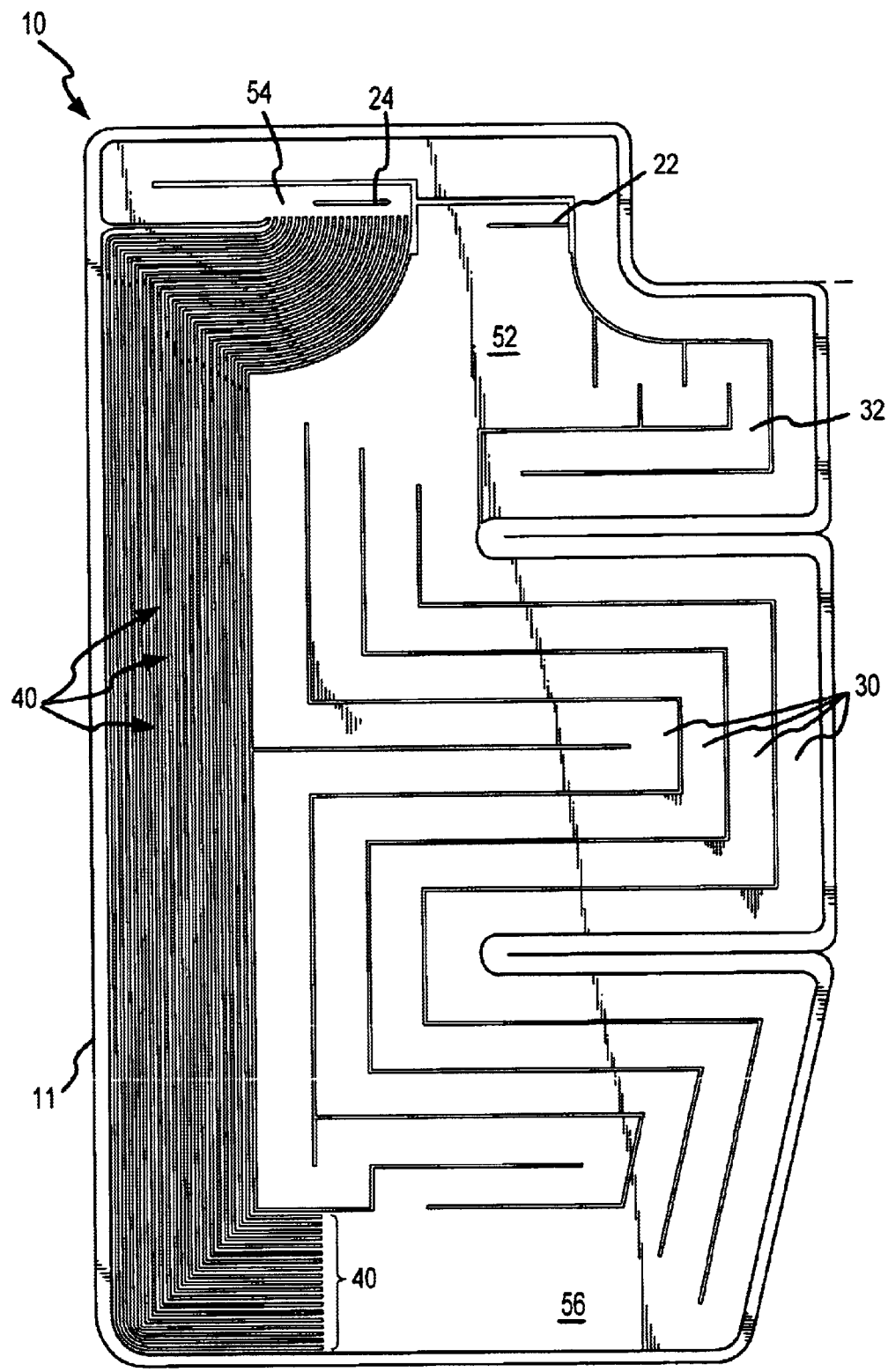
FIG. 2 is an internal plan view of a fluid containing layer of the right back pad comprising the embodiment of FIG. 1.
Figure 3:
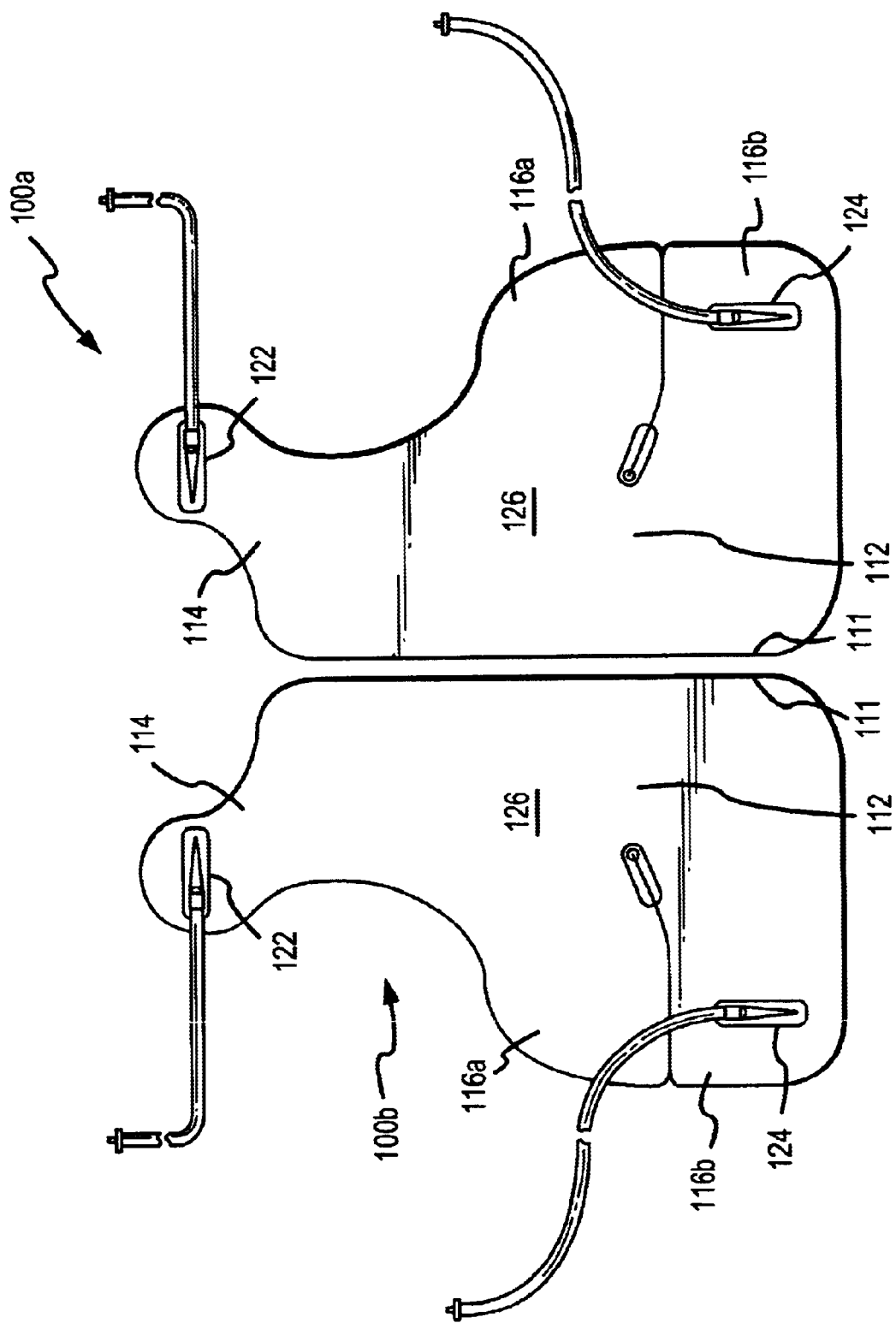
FIG. 3 is a plan view of right and left back pads comprising another embodiment of the present invention.
Figure 4:
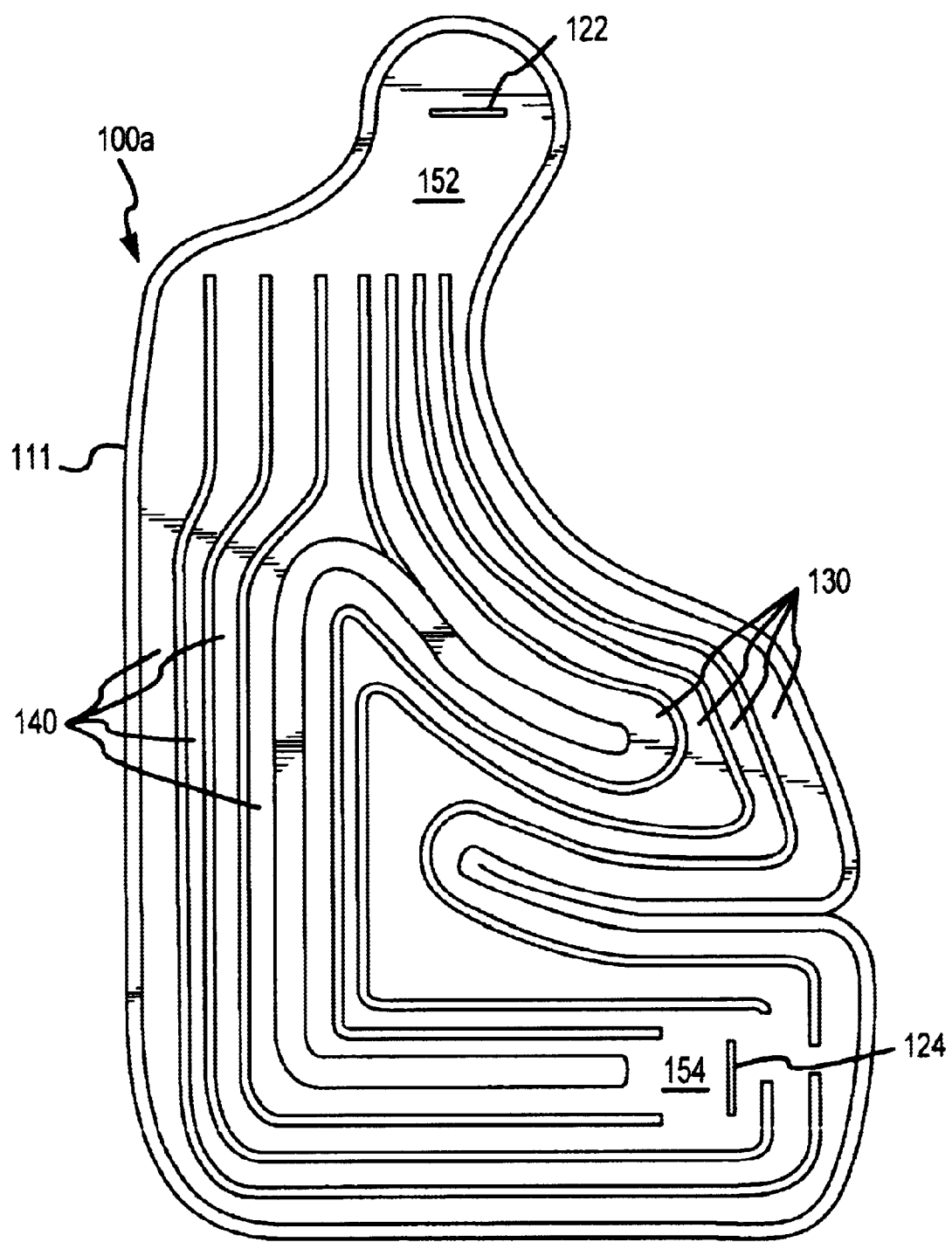
FIG. 4 is an internal plan view of a fluid containing layer of the right back pad comprising the embodiment of FIG. 3.

FIGS. 1 and 2, and FIGS. 3 and 4, correspond with two back pad embodiments 10 and 100, respectively, comprising features of the present invention. The two embodiments will be described in tandem, with differences therebetween identified when appropriate. FIGS. 1 and 3 each show an external plan view of a pair of complimentary back pads 10a, 10b and 100a, 100b, respectively, intended for use on the right and left sides of a patient's back. FIGS. 2 and 4 illustrate certain internal features of back pads 10a and 100a, respectively, wherein such features are the same in reverse orientation within back pads 10b and 100b, respectively.

Before proceeding it should be noted that various aspects of the invention are not limited to back pad applications. By way of example, channeling and segmentation features of the invention may be employed in conjunction with other anatomically configured pads, e.g. pads configured for use on one or both legs and/or the head of a patient.

Figure 5:
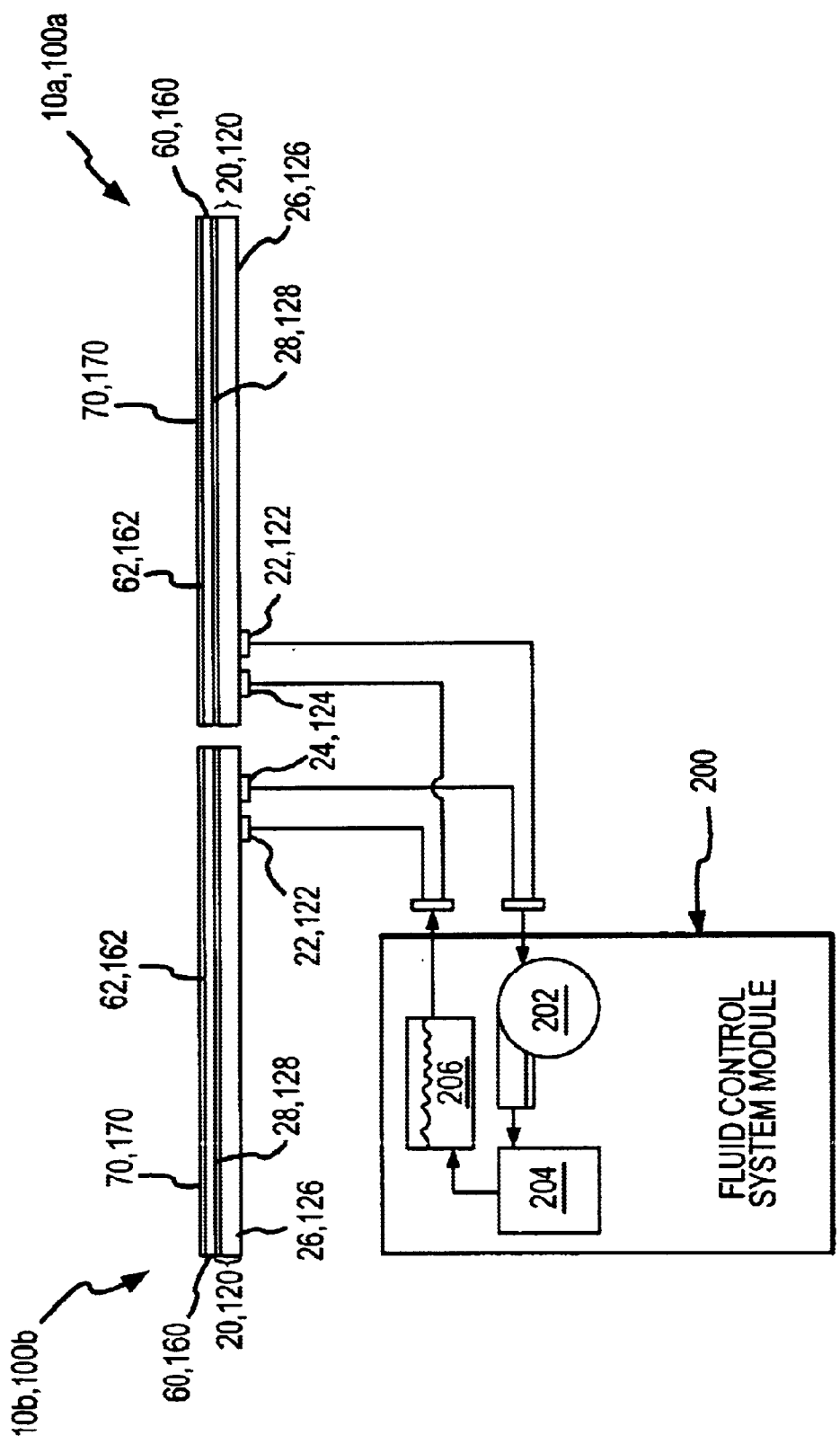
FIG. 5 is a schematic illustration showing the right and left back pads of the embodiments of FIGS. 1, 2 and FIGS. 3, 4 fluidly interconnected with a fluid control system module.

Referring now to the schematic illustration of FIG. 5, the illustrated back pad pairs 10a, 10b and 100a, 100b each include fluid containing layers 20, 120 through which fluid may be circulated during use. That is, fluid may be circulated through fluid ports 22, 24 and 122, 124 of the fluid containing layers 20 and 120, respectively, by an interconnectable fluid control system module 200 (e.g. via interconnected tubing lines). In one arrangement, module 200 includes a pump 202 for drawing fluid through the back pads 10a, 10b or 100a, 100b under negative pressure (e.g. less than about −10 psi), at least one thermal exchange device 204 for heating and/or cooling the circulated fluid, and a fluid reservoir 206.

In addition to a fluid containing layer 20, 120, back pads 10, 100 may each further include a conformable, thermally-conductive layer 60, 160 for contacting the skin of a patient. In this regard, the conformable layer 60, 160 may provide an adhesive surface 62, 162 for enhancing the pad-to-skin interface. Preferably, the adhesive surface 62, 162 extends across a major portion (e.g. substantially all) of the pads 10a, 10b. A release liner 70, 170 may also be provided on the adhesive surface 62, 162 for removal prior to use.

Each of the fluid containing layers 20, 120 may comprise opposing first and second layers 26, 28 and 126, 128, respectively, with a number of fluid channels defined by a plurality of rib members therewithin. More particularly, and as best shown by FIGS. 2 and 4, fluid containing layers 20, 120 may include rib members that define a first plurality of adjacent fluid channels 30, 130 and a second plurality of adjacent fluid channels 40, 140 extending between the fluid ports 22, 24 and 122, 124 of the pads 10 and 100, respectively. As may be appreciated, fluid may be circulated from port 22, 122 to port 24, 124, or alternately from port 24, 124 to port 22, 124.

In the illustrated embodiments, the first plurality of channels 30, 130 are of coincidental, serpentine configuration. More particularly, each of the channels comprising the first plurality of channels 30, 130 is of an S-shaped configuration. Further, such channels 30, 130 may be of a substantially common length, e.g. within about 15% of an average length as measured along their respective center paths. Channels 30, 130 may also have a substantially common average width, e.g. within about 25% of an average of their average widths.

The second plurality of channels 40, 140 are also disposed in a coincidental manner. As illustrated, a major portion of each of the channels comprising the second plurality of channels 40, 140 follows a substantially linear path. Further, it should be noted that channels 40, 140 may be of a substantially common length , e.g. within about 15% of an average length as measured along their respective center paths. Channels 40, 140 may also have a substantially common average width, e.g. within about 25% of an average of their average widths.

Fluid staging chambers 52, 152 and 54, 154 are provided at the fluid ports 22, 122 and 24, 154, respectively. Such staging chambers serve to distribute fluid and normalize fluid flow through the first plurality of channels 30, 130 and second plurality of channels 40, 140.

Additionally, in the back pad 10 of FIG. 1, an intermediate staging chamber 56 is provided between the first plurality of channels 30 and second plurality of channels 40. Such intermediate staging chamber 56 functions to distribute the flow of fluid from one of the first plurality of channels 30 and second plurality of channels 40 to the other, depending on the direction of fluid flow. In this regard, it should be noted that in the back pad 10, a closed fluid flow path between ports 22 and 24 is defined through the first plurality of channels 30, intermediate staging chamber 56 and the second plurality of channels 40.

From an overall configuration standpoint, and with particular reference to FIGS. 1 and 3, back pads 10, 100 are of mirrored configuration, and each include a central segment 12, 112 having a number of flap segments pivotably adjoined thereto. The provision of multiple flap segments facilitates the conformal positioning of back pads 10, 100 about the sides and shoulders of a patient.

In the later regard, back pads 10, 100 each include an end flap segment 14, 114 for conformal positioning between the scapula and top shoulder region of a patient. Further, back pads 10, 100 each include a plurality of side flap segments 16a, 16b, 16c and 116a, 116b, respectively, separated by slits for pivotable, conformable positioning about the sides of a patient. Specifically, the side flap segments 16a, 16b, 16c of back pad 10 are physically separated by slits 18a, 18b, thereby allowing for the separate manipulation of each of the side flap segments 16a, 16b, 16c. For example, side flap segment 16a can be positioned across the upper back to outer shoulder region on a patient, side flap segment 16b may be positioned about the ribcage of a patient, and side flap segment 16c may be positioned about the lower back-to-hip/buttocks region of a patient. Further, it should be noted that the side flap segments 16a, 16b, 16c may be separately detached from or left unattached to a patient during a medical procedure. In particular, the middle flap segment 16b may be manipulated to allow for access to the abdominal region through the ribcage (e.g. for purposes of placing chest drainage tubes or monitoring electrodes).

In order to accommodate the end flap and side flap segments noted above, while also providing for effective thermal exchange with a patient, the configurations and relative widths of the first plurality of channels 30, 130 and second plurality of channels 40, 140, should be further addressed. In particular, and as best shown in FIGS. 3 and 5, the first plurality of channels 30, 130 each include a U-shaped portion extending through the side flap segments 16b, 116a. In pads 10, 100, the pivot axes of the various side flap segments are substantially parallel to the basis of the U-shaped portions of channels 30, 130, as well as the outer side edges of the side flap segments. Further, and with particular respect to back pad 10, it can be seen that an additional channel 32 is configured in a serpentine fashion to pass through side flap segment 16a as well as end flap segment 14.

Referring further to FIGS. 3 and 5, it should be noted that the above-noted linear path portions of the second plurality of channels 40, 140 extend substantially parallel to a side edge 11, 111 of the back pad 10, 100. As may be appreciated, such side edge 11, 111 is intended for positioning substantially parallel to the spine of a patient.

In that regard, in back pad 10 the second plurality of channels 40 have an average channel width that is less than the average channel width of the first plurality of channels 30. More particularly, the average channel width of in the second plurality of channels 40 is at least about 5 times, and more preferably about 10 to 25 times less than the average channel width for the first plurality of channels 30. Such condensed spacing of the channels within the second plurality of channels 40 facilitates support of the second layer 28 over the first layer 26 of the fluid containing layer 20.

Relatedly, it should also be noted that for such support purposes, back pads 10, 100 may include a matrix of support dimples extending between the first and second layers 26, 28 and 126, 128 of the fluid containing layers 20 and 120, respectively. By way of example, such matrix may be defined by offsetting rows and columns of frustoconical dimples which extend from the first layer 26 to the second layer 28.

Figure 8:
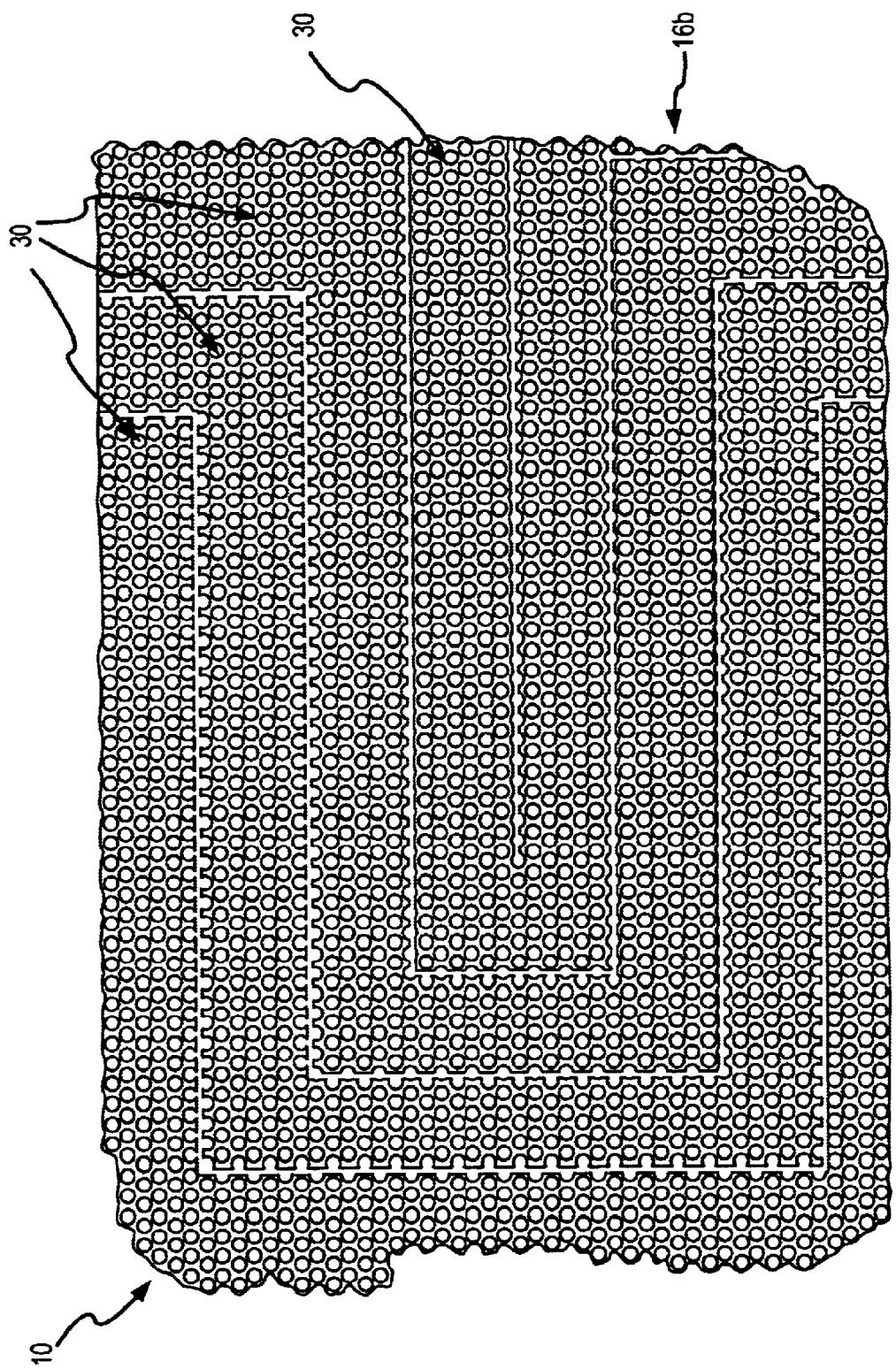
FIG. 8 illustrates a portion of the fluid containing layer shown in FIG. 2.

In back pads 10, 100 the dimple matrix may be provided across the first plurality of channels 30, 130, as well as the fluid staging chambers 52, 152 and 54, 154. Additionally, the dimple matrix may be provided across the intermediate staging chamber 56 and channel 32 of back pad 10. Further, the dimple matrix may also extend across the second plurality of channels 140 in pad 100. FIG. 8 shows an exemplary dimple matrix within a portion of the side flap segment 16b of pad 10.

In one fabrication approach, the first layers 26, 126 of the back pad 10, 100 may comprise a molded foam material that integrally defines the noted dimple matrices as well as the rib members which define the various fluid channels comprising the fluid containing layers 20, 120. Additionally, the molded foam material may define the noted dimple matrices. The second layers 28, 128 of the fluid containing layers 20, 120 may comprise a flexible membrane (e.g. polyolefin, polyurethane, flexible polyvinylchloride) that is sealed around the periphery and across interfacing top end portions of the various ribs and dimples comprising the fluid containing layers 20, 120.

Further, the conformable layer 60, 160 may comprise a first material suspended in a matrix defined by a second material. By way of example, the first material may comprise a liquid and the second material may comprise a polymer. More particularly, conformable layer 60, 160 may comprise a hydrogel that yields an adhesive surface 62, 162 that provides a desirable adhesive and conformable interface with the skin of a patient. As may be appreciated, the utilization of such hydrogel material also facilitates thermal exchange between the fluid containing layer 20, 120 of back pad 10, 100 and a patient.

In relation to the foregoing, it should be noted that the first layers 26, 126, second layers 28, 128, conformable layers 60, 160 and dimple matrices may be provided utilizing the teachings of U.S. Pat. No. 6,197,045 entitled "COOLING/HEATING PAD AND SYSTEM", and U.S. patent application Ser. No. 09/476,850 entitled "COOLING/HEATING PAD AND SYSTEM", filed Jan. 3, 2000, each hereby incorporated by reference in its entirety.

In addition to the above-noted features of back pad 10, 100, a number of optional features may be included. In particular, and with particular reference to FIG. 1, back pad 10 may comprise a number of peripheral adhesive strips 80 each having a selectively removable release liner exposed thereupon. For example, strips 80 may comprise a polyolefin or polyurethane film with hypoallergenic pressure sensitive acrylate adhesive anchored to the pad 10, 100 with a rubber based pressure sensitive adhesive.

As illustrated, adhesive strips 80a, 80b, 80c are located on the side segments 16a, 16b, 16c, respectively, for selective removal upon positioning the back pad 10 on a patient. That is, such adhesive strips 80a, 80b, 80c may be utilized to facilitate the securement of the edges of side flap segment 16a, 16b, 16c to a patient. Similarly, an adhesive strip 80d may be provided along the end flap segment 14 for selective use in securing the end flap segment 14 to a patient.

Further, the location, configuration and orientation of ports 22, 122 and 24, 124 may be selectively established to provide various advantages. In particular, ports 22, 122 and 24, 124 may be provided to avoid patient weight from creating localized high pressure areas on the skin by pressing the port or attached tubing against the skin of a patient. Reducing such high pressure areas reduces any risk of pressure ulcers. Also, the tubing can exit off an operating table without multiple turns, thereby reducing any risk of interconnected tubing buckling/kinking which limits fluid flow.

Figure 9:
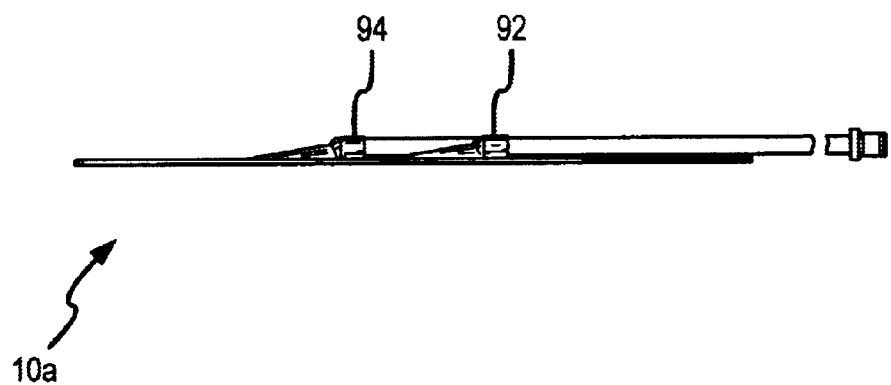
FIG. 9 is a top end view of the right back pad comprising the embodiment of FIG. 1.

Referring in particular to FIGS. 1 and 9, the illustrated ports 22, 24 will now be described in further detail. As shown, ports 22 and 24 are both provided in the end flap segment 14. Further, it can be seen that ports 22 and 24 each include an elongated opening through the first layer 26 into the fluid containing layer 20. Correspondingly, elongated port members 92, 94 are interconnected to the outside, exposed surface of the first layer 26, wherein the elongated openings of ports 22, 24 are in aligned relation with the elongated port members 92, 94. Further in that regard, it can be seen that the center axes for ports 22, 24 and the corresponding port members 92, 94 extend laterally away from the peripheral edge 11 and central segment 12 of the back pad 10 in parallel corelation. As best shown by FIG. 9, the port members 92, 94 are also tapered as they extend laterally outward to accommodate patient comfort considerations and provide a smooth fluid flow transition.

To further facilitate an appreciation of various aspects of the present invention, an exemplary use of back pads 10a, 10b will now be further described with reference to FIGS. 6A, 6B, 6C and 7. Initially, it should be noted that back pads 10a, 10b may be provided in a plurality of different sized sets. As such, use of back pad 10a, 10b may first entail the selection of the best fit set, e.g. based on patient height.

While pads 10a, 10b may be positioned in either order, FIGS. 6A, 6B, 6C illustrate initial positioning of pad 10b. For such positioning, the release liner 70 may be removed from pad 10b and the middle flap segment 16b may be positioned along the mid-axilla of a patient. Then, the bony prominence at the top of the spine of the patient (i.e. protruding just below the neck region) may be located. If the patient is sitting upright, the top edge of the end flap segment 14 of the back pad 10b may be located along a lateral line that extends cross-wise a few inches below the noted bony prominence. If the patient is lying down, such top edge may be placed closer to the lateral line. Of note, if the patient is lying down, the patient may be rolled onto his/her right shoulder during placement of pad 10b.

Next, the upper side flap segment 16a may be lightly positioned on the triceps area of a patient. Further, the pad 10b may be lightly pressed across its lateral extent. At this point, the liners may be removed from the adhesive strips 80b, 80c, 80d, whereupon the adhesive strips are secured to the interfacing skin regions of a patient. Thereafter, the arms of a patient can be tucked to the patient's side and the top side flap segment 16a repositioned thereupon. To maintain such position of segment 16a, the liner may be removed from the adhesive strip 80a and such strip 80a may be secured to the patient's skin.

Following placement of back pad 10b, back pad 10a may be positioned utilizing a similar procedure. If the patient is lying down, the patient may be rolled onto his/her left shoulder before placement of pad 10a. As may be appreciated, back pad 10a may be conveniently overlapped on back pad 10b as necessary along the spinal interface region. Such overlap may be advantageously maintained due to the adhesive surface 62 presented by the conformable layer 60. Such overlap capability facilitates utilization of pads 10a, 10b on a variety of patient sizes.

Figure 7:
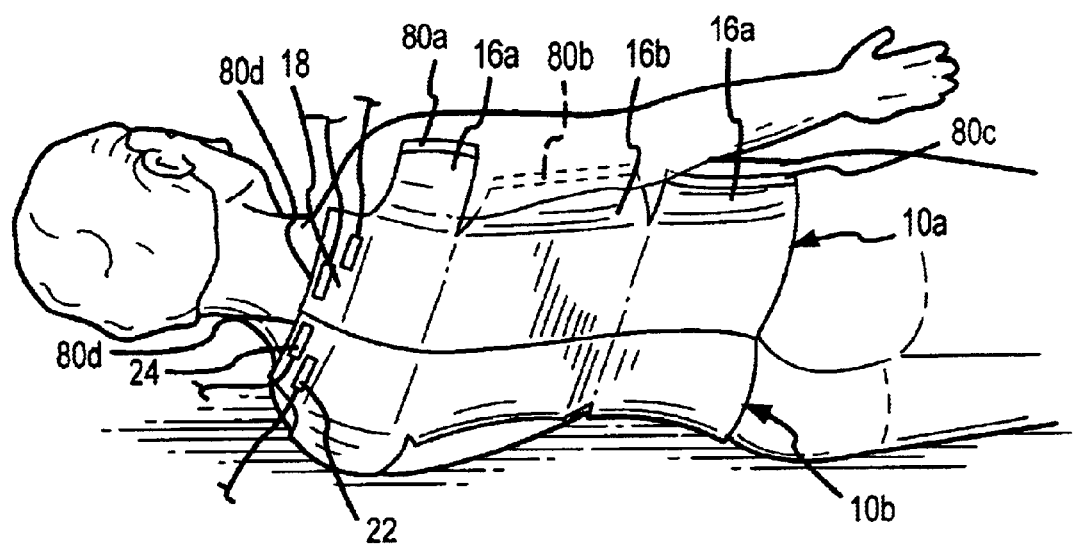
FIG. 7 is a perspective view of the embodiment of FIGS. 1 and 2 as positioned on a prone patient.

As shown in FIG. 7, various pivot axes are provided in relation to the side flaps segments 16a, 16b, 16c and end flap segment 18. In this regard, it may be noted that the pivot axis for end flap segment 18 preferably forms an angle of between about 70° and 110° relative to the pivot axes of side flap segments 16a, 16b, 16c. Such relative orientation of the axes accommodates conformable positioning of the pads 10a, 10b across the various corresponding body regions (e.g. shoulders, rib cage, lower back-to-hip/buttocks regions) which have differing, complex configurations.

As also shown in FIG. 7, positioning of ports 22, 24 in end flap segment 14 allows for ready access thereto and avoids patient discomfort that could result from "sandwiching" of such ports between a patient and a support surface. Further, such positioning directs fluid tubing that is interconnected to ports 22, 24 laterally away from the patient, thereby reducing kinking considerations and otherwise reducing potential obstructions for patient care by medical personnel.

The embodiments described above are for exemplary purposes only and are not intended to limit the scope of the present invention. Various adaptations, modifications and extensions will be apparent to those skilled in the art and are intended to be within the scope of the invention as defined by the claims which follow.

What is claimed:

1. A medical thermal exchange pad, comprising:
   a pliable fluid containing layer for containing a fluid circulated from a first port to a second port of the fluid containing layer;
   a first plurality of adjacent fluid channels, defined within said fluid containing layer, for passing fluid between said first and second ports, wherein said first plurality of fluid channels have first coincidental configurations; and,
   a second plurality of adjacent fluid channels, defined within said fluid containing layer, for passing fluid between said first and second ports, wherein said second plurality of fluid channels have second coincidental configurations different from said first coincidental configurations, and wherein said first and second plurality of fluid channels are fluidly interconnected for series fluid flow therethrough; and,
   an adhesive surface extending over at least a majority of a first side of said fluid containing layer.

2. A medical thermal exchange pad as recited in claim 1, wherein said first plurality of fluid channels have coincidental, serpentine configurations.

3. A medical thermal exchange pad as recited in claim 2, wherein said second plurality of fluid channels each comprise a portion that extends substantially parallel to an edge of said medical thermal exchange pad.

4. A medical thermal exchange pad, comprising:
   a first plurality of adjacent fluid channels, defined within said fluid containing layer, for passing fluid between said first and second ports, wherein said first plurality of fluid channels have first coincidental configurations;
   a second plurality of adjacent fluid channels, defined within said fluid containing layer for passing fluid between said first and second ports, wherein said second plurality of fluid channels have second coincidental configurations different from said first coincidental configurations, wherein said second plurality of fluid channels each comprise a portion that extends substantially parallel to an edge of said medical thermal exchange pad along a substantially linear path, and wherein said first and second plurality of fluid channels are fluidly interconnected for series fluid flow therethrough.

5. A medical thermal exchange pad, comprising:
   a pliable fluid containing layer for containing a fluid circulated from a first port to a second port of the fluid containing layer;
   a first plurality of adjacent fluid channels, defined within said fluid containing layer, for passing fluid between said first and second ports, wherein said first plurality of fluid channels have first coincidental configurations;
   a second plurality of adjacent fluid channels, defined within said fluid containing layer, for passing fluid between said first and second ports, wherein said second plurality of fluid channels have second coincidental configurations different from said first coincidental configurations, and wherein said first and second plurality of fluid channels are fluidly interconnected for series fluid flow therethrough; and,
   an intermediate fluid staging chamber for receiving fluid from said first plurality of fluid channels and distributing said fluid into said second plurality of fluid channels, wherein said first plurality of fluid channels have a corresponding plurality of outlet ends which all terminate at said intermediate fluid staging chamber, and wherein said second plurality of fluid channels have a corresponding plurality of inlet ends which all terminate at said intermediate fluid staging chamber.

6. A medical thermal exchange pad as recited in claim 5, further comprising:
   a first staging chamber, defined within said fluid containing layer, for distributing fluid from said first port to said first plurality of fluid channels, wherein said first plurality of fluid channels have a corresponding plurality of inlet ends which terminate at said first fluid staging chamber.

7. A medical thermal exchange pad, comprising:
   a pliable fluid containing layer for containing a fluid circulated from a first port to a second port of the fluid containing layer;
   a first plurality of adjacent fluid channels, defined within said fluid containing layer, for passing fluid between said first and second ports, wherein said first plurality of fluid channels have first coincidental configurations; and,
   a second plurality of adjacent fluid channels, defined within said fluid containing layer, for passing fluid between said first and second ports, wherein said second plurality of fluid channels have second coincidental configurations different from said first coincidental configurations, and wherein said first and second plurality of fluid channels are fluidly interconnected for series fluid flow therethrough, wherein said first plurality of fluid channels has an average channel width that is about 10 to 25 times greater than an average channel width of said second plurality of fluid channels.

8. A medical thermal exchange pad as recited in claim 7, wherein said first plurality of fluid channels have corresponding channel widths that are substantially maintained along the corresponding lengths thereof, and wherein said second plurality of fluid channels have corresponding channel widths that are substantially maintained along the corresponding lengths thereof.

9. A medical thermal exchange pad as recited in claim 8, wherein said channel widths of said first plurality of channels are substantially equal, and wherein said channel widths of said second plurality of channels are substantially equal.

10. A medical thermal exchange pad, a comprising:
    a pliable fluid containing layer for containing a fluid circulated from a first port to a second port of the fluid containing layer;
    a first plurality of adjacent fluid channels, defined within said fluid containing layer, for passing fluid between said first and second ports, wherein said first plurality of fluid channels have first coincidental configurations; and, a second plurality of adjacent fluid channels, defined within said fluid containing layer, for passing fluid between said first and second ports, wherein said second plurality of fluid channels have second coincidental configurations different from said first coincidental configurations, and wherein said first and second plurality of fluid channels are fluidly interconnected for series fluid flow therethrough, wherein said first plurality of fluid channels has an average channel width that is at least about 5 times greater than an average channel width of the second plurality of fluid channels.

11. A medical thermal exchange pad as recited in claim 10, wherein said first plurality of fluid channels have corresponding channel lengths that are substantially equal, and wherein said second plurality of fluid channels have corresponding channel lengths that are substantially equal.

12. A medical thermal exchange pad as recited in claim 10, said fluid containing layer being defined by opposing top and bottom layers, and said plurality of fluid channels being defined by a plurality of rib members adjoined to and between said opposing top and bottom layers.

13. A medical thermal exchange pad as recited in claim 12, wherein said plurality of rib members are integrally defined by said bottom layer.

14. A medical thermal exchange pad as recited in claim 13, wherein said top layer is defined by a flexible film.

15. A medical thermal exchange pad as recited in claim 14, wherein said bottom layer further defines a matrix of upstanding dimples, and wherein said matrix of dimples extends across said first plurality of fluid channels.

16. A medical thermal exchange pad as recited in claim 10, further comprising:
an adhesive surface extending over at least a portion of a first side of said fluid containing layer.

17. A medical thermal exchange pad as recited in claim 16, further comprising:
a conformable layer disposed on said first side of the fluid containing layer, said conformable layer being thermally-conductive and defining said adhesive surface.

18. A medical thermal exchange pad as recited in claim 17, wherein said conformable layer comprises:
a first material suspended in a matrix defined by a second material.

19. A medical thermal exchange pad as recited in claim 18, wherein said first material comprises a liquid and said second material comprises a polymer.

20. A medical thermal exchange pad, comprising:
a pliable fluid layer for containing a fluid circulated from a first port to a second port of the fluid containing layer;
a first plurality of adjacent fluid channels, defined within said fluid containing layer, for passing fluid between said first and second ports;
a second plurality of adjacent fluid channels, defined within said fluid containing layer, for passing fluid between said first and second ports; and,
an intermediate fluid staging chamber, for receiving fluid from one of said first and second plurality of fluid channels and distributing said fluid into the other of said first and second plurality of fluid channels, wherein the first plurality of fluid channels have a corresponding plurality of outlet ends which all terminate at said intermediate fluid staging chamber, and wherein said second plurality of fluid channels have a corresponding plurality of inlet ends which all terminate at said intermediate fluid staging chamber.

21. A medical thermal exchange pad as recited in claim 20, further comprising:
a first staging chamber, defined within said fluid containing layer, for distributing fluid from said first port to said first plurality of fluid channels, wherein said first plurality of fluid channels have a corresponding plurality of inlet ends which terminate at said first staging chamber.

22. A medical thermal exchange pad as recited in claim 20, wherein said first plurality of fluid channels have first coincidental configurations, and wherein said second plurality of fluid channels have second coincidental configurations different than said first coincidental configurations.

23. A medical thermal exchange pad as recited in claim 22, wherein said first plurality of fluid channels have coincidental, serpentine configurations.

24. A medical thermal exchange pad as recited in claim 23, wherein said second plurality of fluid channels each comprise a portion that extends substantially parallel to an edge of said medical thermal exchange pad.

25. A medical thermal exchange pad as recited in claim 24, wherein said portions of said second plurality of fluid channel each follow a substantially linear path.

26. A medical thermal exchange pad, comprising:
a central segment, at least one side flap segment pivotably interconnected to the central segment, and at least one end-flap segment pivotably interconnected to the central segment;
a pliable fluid containing layer for containing a fluid circulated from an inlet port to an outlet port of the fluid containing layer, wherein said inlet port and outlet port are both located in said end-flap segment; and,
a plurality of adjacent fluid channels defined within said fluid containing layer.

27. A medical thermal exchange pad as recited in claim 26, said plurality of fluid channels including:
a first plurality of fluid channels; and,
a second plurality of fluid channels, wherein said first and second plurality of fluid channels are fluidly interconnected for series fluid flow therethrough.

28. A medical thermal exchange pad as recited in claim 27, wherein said inlet port and outlet port extend in substantially parallel co-relation.

29. A medical thermal exchange pad as recited in claim 28, wherein said inlet and outlet ports include inlet and outlet port members, respectively, said inlet and outlet port members each being of a tapered configuration.

30. A medical thermal exchange pad as recited in claim 28, wherein said inlet and outlet ports are oriented substantially parallel to a pivot axis of said end-flap segment.

31. A medical thermal exchange pad as recited in claim 27, wherein said first plurality of fluid channels have coincidental, serpentine configurations and extend through said at least one side flap segment.

32. A medical thermal exchange pad as recited in claim 31, wherein said second plurality of fluid channels each comprise a portion that extends substantially parallel to an edge of said medical thermal exchange pad.

33. A medical thermal exchange pad, comprising:
a central segment and a plurality side flap segments separately and pivotably interconnected to the central segment;
a pliable fluid layer for containing a fluid circulated from an inlet port to an outlet port of the fluid containing layer;
a first plurality of adjacent, serpentine fluid channels defined with said fluid containing layer, wherein said first plurality of fluid channels extend through first and second ones of said plurality of side flap segments; and, at least another fluid channel defined within said fluid containing layer, wherein said at least another fluid channel extends through a third one of said plurality of side flap segments.

34. A medical thermal exchange pad as recited in Claim 33, wherein said medical thermal exchange pad further includes at least one end flap segment pivotably interconnected to a central segment, and wherein said another fluid channel extends through said at least one end flap segment.

35. A medical thermal exchange pad, comprising:

a pliable fluid containing layer for containing a fluid circulated from a first port to a second port of the fluid containing layer;

a first plurality of adjacent fluid channels, defined within said fluid containing layer, for passing fluid between said first and second ports, wherein said first plurality of fluid channels have first coincidental, serpentine configurations and are non-communicating between their respective inlet and outlet ends; and, a second plurality of adjacent fluid channels, defined within said fluid containing layer, for passing fluid between said first and second ports, wherein said second plurality of fluid channels have second coincidental configurations different from said first coincidental configurations, and wherein said first and second plurality of fluid channels are fluidly interconnected for series fluid flow therethrough.

36. A medical thermal exchange pad as recited in claim 35, wherein second plurality of fluid channels are non-communicating between their respective inlet and outlet ends.

37. A medical thermal exchange pad as recited in claim 35, wherein said second plurality of fluid channels each comprise a portion that extends substantially parallel to an edge of said medical thermal exchange pad.

* * * * *